(12) United States Patent
Falcó et al.

(10) Patent No.: US 8,227,501 B2
(45) Date of Patent: Jul. 24, 2012

(54) 1,6-DIHYDRO-2H-3-OXA-6-AZA-AS-INDACENE COMPOUNDS

(75) Inventors: José L. Falcó, Barcelona (ES); Albert Palomer, Barcelona (ES); Antonio Guglietta, Molins de Rei (ES)

(73) Assignee: Ferrer Internacional, S.A., Barcelona (ES)

( * ) Notice: Subject to any disclaimer, the term of this patent is extended or adjusted under 35 U.S.C. 154(b) by 0 days.

(21) Appl. No.: 13/056,492

(22) PCT Filed: Jul. 29, 2009

(86) PCT No.: PCT/EP2009/059829
§ 371 (c)(1),
(2), (4) Date: Jan. 28, 2011

(87) PCT Pub. No.: WO2010/012789
PCT Pub. Date: Feb. 4, 2010

(65) Prior Publication Data
US 2011/0144178 A1    Jun. 16, 2011

(30) Foreign Application Priority Data

Jul. 30, 2008 (EP) .................................... 08161485

(51) Int. Cl.
C07D 491/048 (2006.01)
A61K 31/407 (2006.01)
(52) U.S. Cl. ........................................ 514/411; 548/430
(58) Field of Classification Search .................. None
See application file for complete search history.

(56) References Cited

U.S. PATENT DOCUMENTS

| | | | |
|---|---|---|---|
| 4,600,723 | A | 7/1986 | Short et al. |
| 4,665,086 | A | 5/1987 | Short et al. |
| 5,276,051 | A | 1/1994 | Lesieur et al. |
| 5,308,866 | A | 5/1994 | Lesieur et al. |
| 5,633,276 | A | 5/1997 | North et al. |
| 5,708,005 | A | 1/1998 | Ohkawa et al. |
| 6,034,239 | A | 3/2000 | Ohkawa et al. |
| 6,143,789 | A | 11/2000 | Lefoulon et al. |
| 6,310,074 | B1 | 10/2001 | Depreux et al. |
| 6,583,319 | B1 | 6/2003 | Langlois et al. |
| 6,737,431 | B2 | 5/2004 | Takaki et al. |
| 6,908,931 | B2 | 6/2005 | Dubowchik et al. |
| 7,235,550 | B2 | 6/2007 | Guillaumet et al. |
| 7,297,711 | B2 | 11/2007 | Jasti et al. |

FOREIGN PATENT DOCUMENTS

| | | |
|---|---|---|
| EP | 0 848 888 B1 | 10/2001 |
| EP | 1 214 944 A1 | 6/2002 |
| WO | WO 89/01472 A1 | 2/1989 |
| WO | WO 95/17405 A1 | 6/1995 |
| WO | WO 97/32871 A1 | 9/1997 |
| WO | WO 2005/062992 A2 | 7/2005 |

OTHER PUBLICATIONS

Altun, et al. Int. J. Clin. Prac. 5:835-45 (2007) (Abstract).*
Hardeland, et al. Arzneimittelforschung, 58:1-10 (2008) (Abstract).*
Arendt, et al. Brit. J. Psy. 193:267-9 (2008).*
Morissette, et al. Adv. Drug. Del. Rev. 56:275 (2004).*
Rouhi, Chem. & Eng. News, Feb. 24, 2003, 81(8), 32-35.*
Byrn et al. Solid-State Chemistry of Drugs, 2d, Chapter 11:Hydrates and Solvates, 233 247 (1999).*
Hörig et al., J. Translational Med. 2:44 (2004).*
International Search Report for PCT/EP2009/059829, dated Oct. 21, 2009.
Li-Qiang Sun et al.; (R)-2-(4-Phenylbutyl)dihydrobenzofuran derivatives as meiatoninergic agents; Bioorganic & Medicinal Chemistry Letters; No. 15; pp. 1345-1349, 2005.
Osamu Uchikawa et al.; Synthesis of a Novel Series of Tricyclic Indan Derivatives as Melatonin Receptor Agonists; J. Med. Chem.; No. 45; pp. 4222-4239, 2002.
Seithikurippu R. Pandi-Perumal et al.; Drug Insight: the use of melatonergic agonists for the treatment of insommnia—focus on ramelteon; National Clinical Practice Neurology; vol. 3; No. 4; pp. 221-228; Apr. 2007.

* cited by examiner

*Primary Examiner* — Yong Chu
*Assistant Examiner* — Michael Barker
(74) *Attorney, Agent, or Firm* — Birch, Stewart, Kolasch & Birch, LLP

(57) ABSTRACT

The invention provides new compounds of formula (I) wherein $R_1$, $R_2$, $R_3$, $R_4$, and X have different meanings. Preparative processes, pharmaceutical compositions, and uses thereof in the treatment or prevention of conditions mediated by melatonin receptors are also provided.

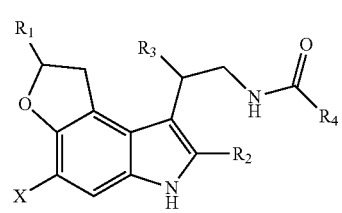

19 Claims, No Drawings

1,6-DIHYDRO-2H-3-OXA-6-AZA-AS-INDACENE COMPOUNDS

TECHNICAL FIELD

The invention is directed to compounds with high affinity on melatonin receptors, specifically 1,6-dihydro-2H-3-oxa-6-aza-as-indacene compounds, and more specifically N-carbonyl compounds of 2-(1,6-dihydro-4-halo-2H-3-oxa-6-aza-as-indacen-8-yl)-ethylamine.

BACKGROUND ART

Insomnia is a very common disorder, affecting from 20 to 40% of the adult population, with an increasing incidence in the elderly. Insomnia can be due to many causes. One of them is the disturbance of the normal regulating sleep-wake cycles. This asynchrony can result in pathological changes. A potential therapeutic treatment to alleviate this effect consists in re-synchronizing the sleep-wake cycles by modulating the melatonergic system (Li-Qiang Sun, Bioorganic & Medicinal Chemistry Letters 2005, 15, 1345-49).

Melatonin is a hormone secreted by the pineal gland in mammals being produced at night to aid the body in regulating sleep-wake cycles, and it is also responsible for the photoperiodic information, and for the modulation of the retina physiology. The secretion of melatonin in humans occurs simultaneously to nocturnal sleep, and the increase of melatonin levels is correlated with the increase of somnolence at nightfall. The amount of melatonin the body produces decreases with age, which may explain why the elderly suffer from insomnia more frequently than the general population. The therapeutic uses of melatonin in humans embrace the treatment of sleep delay syndrome and jetlag, including the treatment of nocturnal workers, and as hypnotic by itself. However, its short half-life (minutes) limits its therapeutic use. The synthesis of melatonin and the nocturnal secretion thereof are controlled by the supraquiasmatic nucleus, and are synchronized by the environmental light (Osamu Uchikawa et al., J. Med. Chem. 2002, 45, 4222-39; Pandi-Perumal et al., Nature Clinical Practice 2007, 3 (4), 221-228).

Melatonin receptors have been classified as MT1, MT2, and MT3, on the basis of pharmacological profiles. MT1 receptor is localized in the hypothalamic Central Nervous System, while MT2 receptor is distributed in the Central Nervous System and in the retina. The presence of MT1 and MT2 receptors has been disclosed also at peripheral level. MT1 and MT2 receptors are involved in a large number of conditions, such as depression, stress, sleep disorders, anxiety, seasonal affective disorders, cardiovascular pathology, pathology of the digestive system, insomnia or fatigue due to jetlag, schizophrenia, panic attack, melancholia, appetite disorders, obesity, insomnia, psychotic disorders, epilepsy, diabetes, Parkinson's disease, senile dementia, disorders associated with normal or pathological ageing, migraine, memory loss, Alzheimer's disease and cerebral circulation disorders. The MT3 receptor has been characterized as homologous to the quinone reductase-2 (QR2) enzyme. MT1 y MT2 receptors are coupled to G-Protein-coupled Receptor (GPCR) whose stimulation by an agonist produces a decrease in the adenylate cyclase activity and a subsequent decrease in the intracellular cAMP.

Synthetic melatonin receptors agonists have been object of intense research in recent years. In addition to its first use for insomnia, they may have potential application in the synchronization of disturbed circadian rhythms, sleep disturbances in the elderly, seasonal depression and jetlag, among many others. Furthermore, it has been shown that melatonin receptor agonists do not induce any of the hypothermic, hypotensive or bradycardic effects caused by melatonin in humans.

Ramelteon, N-[2-[(8S)-1,6,7,8-tetrahydro-2H-indeno[5,4-b]furan-8-yl)ethyl]propionamide, has been the first melatonin receptors agonist approved by the US Food and Drug Administration (FDA) for therapeutic use in insomnia with no time limitation. Its mechanism of action is based on the agonism on MT1 and MT2 receptors. Ramelteon has no selectivity upon MT1 and MT2 receptors; however it shows selectivity on other central and peripheral receptors. $K_i$ is 0.014 nM for MT1 and 0.045 nM for MT2. It shows a good absorption but suffers from an important metabolic first pass, being biotransformed in four metabolites.

Patent documents U.S. Pat. No. 4,600,723 and U.S. Pat. No. 4,665,086 disclose the use of melatonin to minimize the variations of the circadian rhythms induced by changes in the working schedules or the quick transit through diverse time zones (jetlag). Some compound series with melatonergic activity have been disclosed in patent documents EP848699B1, U.S. Pat. No. 5,276,051, U.S. Pat. No. 5,308,866, U.S. Pat. No. 5,633,276, U.S. Pat. No. 5,708,005, U.S. Pat. No. 6,143,789, U.S. Pat. No. 6,310,074, U.S. Pat. No. 6,583,319, U.S. Pat. No. 6,737,431, U.S. Pat. No. 6,908,931, U.S. Pat. No. 7,235,550, U.S. Pat. No. 7,297,711, WO8901472 and WO2005062992.

U.S. Pat. No. 6,034,239 discloses tricyclic melatonergic compounds of formula:

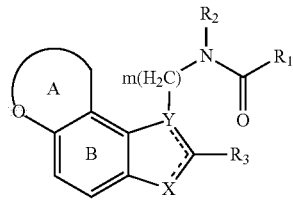

wherein A, B, m, $R_1$, $R_2$, $R_3$, X, and Y have the meanings there indicated. Ramelteon belongs to this structure when A=$(CH_2)_2$, B has no additional substituents, $R_1$=ethyl, $R_2$=$R_3$=H, m=2, X=$CH_2$, Y=CH, dotted bonds are saturated bonds, and Y shows (S)— configuration (examples 19 and 20).

The approval of ramelteon represents an important milestone for the proof of concept of the melatonin target, and has opened new possibilities for research. However, there is an increasing need for new compounds with improved properties, such as higher potency and an increased resistance to metabolism, in order to provide more efficient treatments of conditions mediated by melatonin receptors.

SUMMARY OF THE INVENTION

Surprisingly the present invention provides potent active compounds showing a better agonism for the MT1 receptor in comparison with ramelteon and melatonin. For instance, examples 14 and 18 have, respectively, an agonism (at 1 nM) of 55.1 and 59.8%. Nor ramelteon neither melatonin have those levels of agonism. Respectively, ramelteon and melatonin have 47.4 and 48.0% at such concentration.

In a first aspect the present invention refers to a compound of formula I,

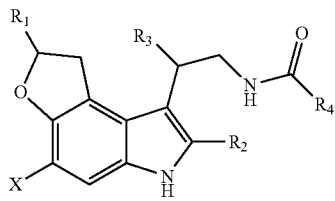

in free or pharmaceutically acceptable salt, solvate, hydrate, or enantiomeric form, wherein:
$R_1$ is selected from the group consisting of hydrogen, linear or branched (1-6C)alkyl, and (3-6C)cycloalkyl;
$R_2$ is selected from the group consisting of hydrogen, halogen selected from chlorine and bromine, phenyl, phenyl(1-2C)alkyl, COOH, and $COOR_5$;
$R_3$ is selected from the group consisting of hydrogen, linear or branched (1-6C)alkyl, and (3-6C)cycloalkyl;
$R_4$ is selected from the group consisting of linear or branched (1-6C)alkyl, (3-6C)cycloalkyl, $CHFCH_3$, $CF_3$, OH, $OR_6$, $NH_2$, and $NHR_7$;
$R_5$ is selected from the group consisting of linear or branched (1-6C)alkyl, phenyl, phenyl(1-2C)alkyl, and (3-6C)cycloalkyl;
$R_6$ is selected from the group consisting of linear or branched (1-6C)alkyl, and (3-6C)cycloalkyl;
$R_7$ is selected from the group consisting of linear or branched (1-6C)alkyl, and (3-6C)cycloalkyl; and
X is a halogen atom selected from the group consisting of fluorine, and chlorine.

In a second aspect the present invention refers to a process for preparing a compound of formula I in free or pharmaceutically acceptable salt, solvate, hydrate, or enantiomeric form that comprises:
i) a) reacting a compound of formula XII,

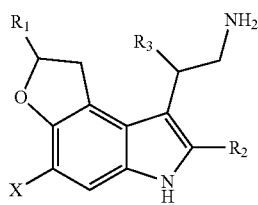

wherein $R_1$, $R_2$, $R_3$, and X are as defined herein, with a coupling agent selected from the group consisting of:
a) an acyl chloride of formula $R_4$—COCl, in which case $R_4$ represents linear or branched (1-6C)alkyl, (3-6C)cycloalkyl, $CHFCH_3$, or $CF_3$; b) a chloroformate of formula $R_4$—COCl, in which case $R_4$ represents $OR_6$, wherein $R_6$ is as described herein; and c) an isocyanate of formula $R_4$=CO, in which case $R_4$ represents $NR_7$, wherein $R_7$ is as described herein; and
b) hydrolyzing, if desired, the resultant compound of formula I when $R_4$ is $OR_6$ or $NHR_7$ to OH or $NH_2$ respectively; and
ii) recovering the resultant compound of formula I in free or pharmaceutically acceptable salt, solvate, hydrate, or enantiomeric form.

In a third aspect the present invention refers to a pharmaceutical composition comprising a therapeutically effective amount of the compound of formula I according to the first aspect of the invention, and a suitable carrier.

In a fourth aspect the present invention refers to a compound of formula I according to the first aspect of the invention, for use as a medicament.

In a fifth aspect the present invention refers to a compound of formula I according to the first aspect of the invention, for use in the treatment or prevention of conditions associated with a disturbed functioning of systems regulated by melatonin.

In a sixth aspect the present invention refers to a compound of formula I according to the first aspect of the invention, for use in the treatment or prevention of depression, stress, sleep disorders, anxiety, seasonal affective disorders, cardiovascular pathology, pathology of the digestive system, insomnia or fatigue due to jetlag, schizophrenia, panic attack, melancholia, appetite disorders, obesity, insomnia, psychotic disorders, epilepsy, diabetes, Parkinson's disease, senile dementia, disorders associated with normal or pathological ageing, migraine, memory loss, Alzheimer's disease or cerebral circulation disorders.

In a seventh aspect the present invention refers to a use of a compound of formula I according to the first aspect of the invention for the manufacture of a medicament for the treatment or prevention of conditions associated with a disturbed functioning of systems regulated by melatonin.

In a eighth aspect the present invention refers to a use of a compound of formula I according to the first aspect of the invention for the manufacture of a medicament for the treatment or prevention of depression, stress, sleep disorders, anxiety, seasonal affective disorders, cardiovascular pathology, pathology of the digestive system, insomnia or fatigue due to jetlag, schizophrenia, panic attack, melancholia, appetite disorders, obesity, insomnia, psychotic disorders, epilepsy, diabetes, Parkinson's disease, senile dementia, disorders associated with normal or pathological ageing, migraine, memory loss, Alzheimer's disease or cerebral circulation disorders.

An object of this invention is to provide a novel method to treat or prevent conditions associated with a disturbed functioning of systems regulated by melatonin.

Another object of this invention is to provide a novel method to treat or prevent depression, stress, sleep disorders, anxiety, seasonal affective disorders, cardiovascular pathology, pathology of the digestive system, insomnia or fatigue due to jetlag, schizophrenia, panic attack, melancholia, appetite disorders, obesity, insomnia, psychotic disorders, epilepsy, diabetes, Parkinson's disease, senile dementia, disorders associated with normal or pathological ageing, migraine, memory loss, Alzheimer's disease, or cerebral circulation disorders in a mammal, including a human, by administering a pharmaceutically effective amount of a compound of formula I or a pharmaceutically acceptable salt, solvate, hydrate, or enantiomeric form thereof.

DETAILED DESCRIPTION OF THE INVENTION

The term "pharmaceutically acceptable salt" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic, tartaric acids, and the like, and any salt formed from organic and inorganic bases, such as the alkali metal and alkaline earth metal salts, especially the sodium and potassium salts, ammonium salts and salts of amines, including lower alkylamines, such as methylamine, ethylamine, trimethylamine and the like, hydroxyloweralkylamines, such as ethanolamine and diethanolamine, and heterocyclic amines, such as morpholine and piperazine.

According to a particular embodiment, $R_1$ is hydrogen or linear or branched (1-6C)alkyl, such as methyl.

According to a further particular embodiment, $R_2$ is hydrogen.

According to a further particular embodiment, $R_3$ is hydrogen or linear or branched (1-6C)alkyl, such as methyl.

According to a further particular embodiment, $R_4$ is linear or branched (1-6C)alkyl, in particular (1-4C)alkyl, such as methyl, ethyl, propyl, i-propyl or butyl, or (3-6C)cycloalkyl, such as c-propyl, $CF_3$ or $CHFCH_3$, with methyl, ethyl or $CF_3$ being a further particular embodiment.

According to a further particular embodiment, $R_5$ is linear or branched (1-6C)alkyl, such as methyl.

According to a further particular embodiment, $R_6$ is linear or branched (1-6C)alkyl, such as methyl or ethyl.

According to a further particular embodiment, $R_7$ is linear or branched (1-6C)alkyl, such as methyl or ethyl.

According to a further particular embodiment, X is fluorine.

In a preferred embodiment, the present invention refers to a compound according to the first aspect of the invention wherein $R_1$ is selected from the group consisting of hydrogen and methyl, $R_3$ is selected from the group consisting of hydrogen and methyl, $R_5$ is methyl, $R_6$ is selected from the group consisting of methyl and ethyl, $R_7$ is selected from the group consisting of methyl and ethyl, and X is fluorine, $R_2$ and $R_4$ being as defined herein.

In a preferred embodiment, the present invention refers to a compound according to the first aspect of the invention wherein $R_1$ is selected from the group consisting of hydrogen and methyl, $R_2$ is hydrogen, $R_3$ is selected from the group consisting of hydrogen and methyl, $R_4$ is selected from the group consisting of methyl, ethyl, propyl, i-propyl, c-propyl, butyl, $CF_3$ and $CHFCH_3$ (methyl, ethyl or $CF_3$ being particularly preferred), and X is fluorine.

Preferably, the compound according to the first aspect of the invention is selected from the group consisting of:

N-[2-(4-Fluoro-1,6-dihydro-2H-3-oxa-6-aza-as-indacen-8-yl)-ethyl]-acetamide;
N-[2-(4-Fluoro-1,6-dihydro-2H-3-oxa-6-aza-as-indacen-8-yl)-ethyl]-propionamide;
N-[2-(4-Fluoro-1,6-dihydro-2H-3-oxa-6-aza-as-indacen-8-yl)-ethyl]-butyramide;
N-[2-(4-Fluoro-1,6-dihydro-2H-3-oxa-6-aza-as-indacen-8-yl)-ethyl]-isobutyramide;
Cyclopropanecarboxylic acid [2-(4-fluoro-1,6-dihydro-2H-3-oxa-6-aza-as-indacen-8-yl)-ethyl]-amide;
2,2,2-Trifluoro-N-[2-(4-fluoro-1,6-dihydro-2H-3-oxa-6-aza-as-indacen-8-yl)-ethyl]-acetamide;
N-[2-(4-Fluoro-2-methyl-1,6-dihydro-2H-3-oxa-6-aza-as-indacen-8-yl)-propyl]-propionamide;
N-[2-(4-Fluoro-2-methyl-1,6-dihydro-2H-3-oxa-6-aza-as-indacen-8-yl)-propyl]-acetamide;
N-[2-(4-Fluoro-2-methyl-1,6-dihydro-2H-3-oxa-6-aza-as-indacen-8-yl)-ethyl]-acetamide;
N-[2-(4-Fluoro-2-methyl-1,6-dihydro-2H-3-oxa-6-aza-as-indacen-8-yl)-ethyl]-propionamide;
N-[2-(4-Fluoro-2-methyl-1,6-dihydro-2H-3-oxa-6-aza-as-indacen-8-yl)-ethyl]-butyramide;
Pentanoic acid [2-(4-fluoro-2-methyl-1,6-dihydro-2H-3-oxa-6-aza-as-indacen-8-yl)-ethyl]-amide;
Cyclopropanecarboxylic acid [2-(4-fluoro-2-methyl-1,6-dihydro-2H-3-oxa-6-aza-as-indacen-8-yl)-ethyl]-amide;
2,2,2-Trifluoro-N-[2-(4-fluoro-2-methyl-1,6-dihydro-2H-3-oxa-6-aza-as-indacen-8-yl)-ethyl]-acetamide;
2-Fluoro-N-[2-(4-fluoro-2-methyl-1,6-dihydro-2H-3-oxa-6-aza-as-indacen-8-yl)-ethyl]-propionamide;
Cyclopropanecarboxylic acid [2-(4-fluoro-2-methyl-1,6-dihydro-2H-3-oxa-6-aza-as-indacen-8-yl)-propyl]-amide;
2,2,2-Trifluoro-N-[2-(4-fluoro-2-methyl-1,6-dihydro-2H-3-oxa-6-aza-as-indacen-8-yl)-propyl]-acetamide; and
2-Fluoro-N-[2-(4-fluoro-2-methyl-1,6-dihydro-2H-3-oxa-6-aza-as-indacen-8-yl)-propyl]-propionamide.

The compounds of the general formula I may be prepared by i) a) reacting a compound of formula XII,

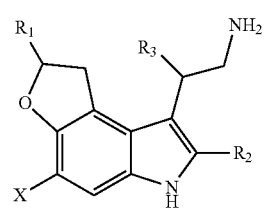

XII wherein $R_1$, $R_2$, $R_3$, and X are as defined herein, with a coupling agent selected from the group consisting of:
a) an acyl chloride of formula $R_4$—COCl, in which case $R_4$ represents linear or branched (1-6C)alkyl, (3-6C)cycloalkyl, $CHFCH_3$, or $CF_3$; b) a chloroformate of formula $R_4$—COCl, in which case $R_4$ represents $OR_6$, wherein $R_6$ is as described herein; and c) an isocyanate of formula $R_4$=CO, in which case $R_4$ represents $NR_7$, wherein $R_7$ is as described herein; and b) hydrolyzing, if desired, the resultant compound of formula I when $R_4$ is $OR_6$ or $NHR_7$ to OH or $NH_2$ respectively; and ii) recovering the resultant compound of formula I in free or pharmaceutically acceptable salt, solvate, hydrate, and enantiomeric form.

The compounds of the present invention when $R_1$=$R_2$=$R_3$=H, and X=F can be prepared from 2-fluoro-4-nitro-phenol, 1, according to Scheme 1. Final step is generalized for all meanings of $R_1$, $R_2$, $R_3$, and X, and a selection of meanings for $R_4$ comprising: a) linear or branched (1-6C) alkyl, (3-6C)cycloalkyl, $CHFCH_3$, and $CF_3$; b) $OR_6$, wherein $R_6$ is as described herein; and c) $NHR_7$, wherein $R_7$ is as described herein.

Scheme 1

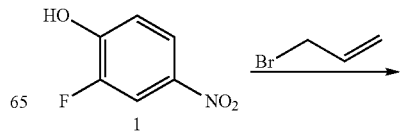

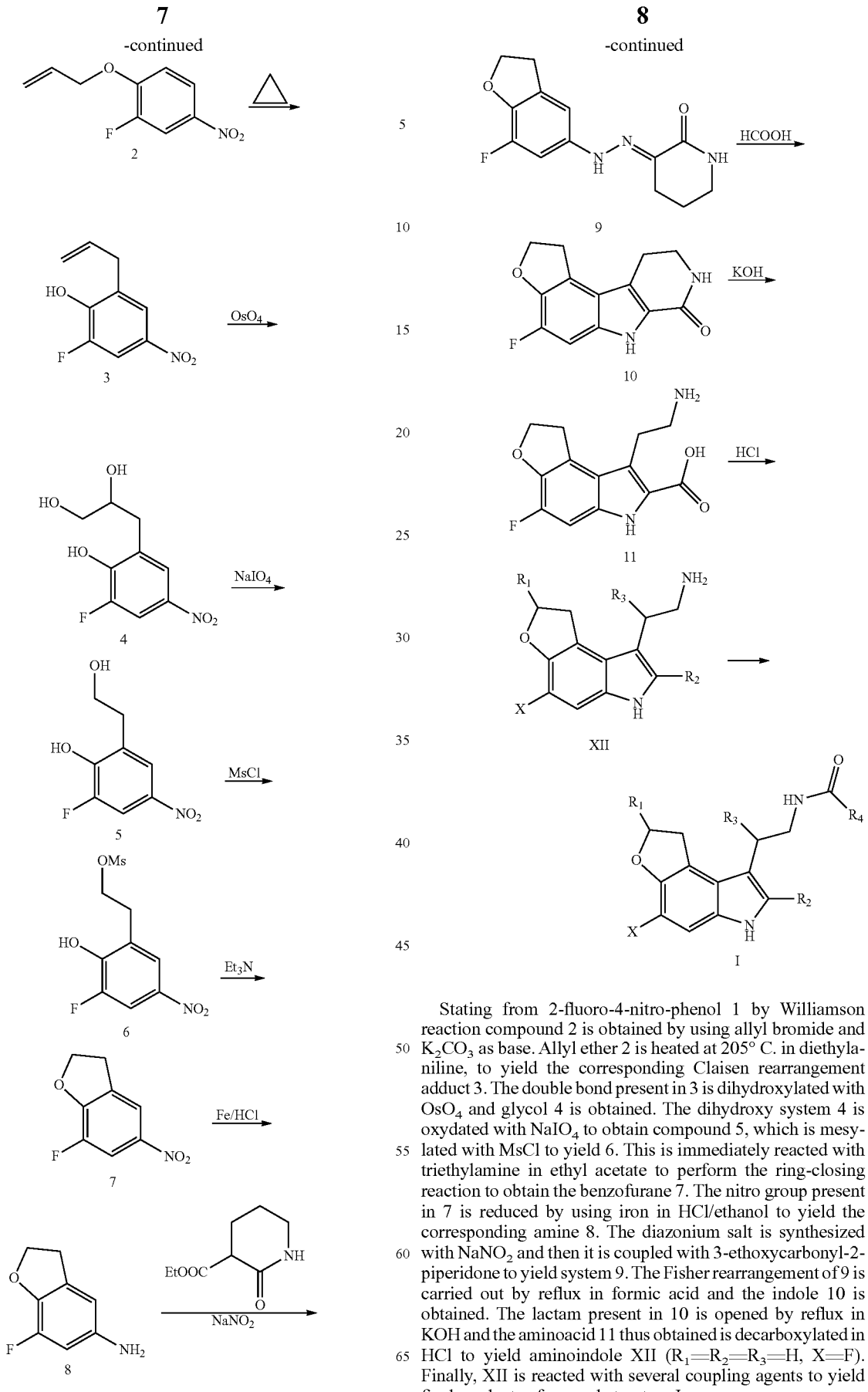

Stating from 2-fluoro-4-nitro-phenol 1 by Williamson reaction compound 2 is obtained by using allyl bromide and $K_2CO_3$ as base. Allyl ether 2 is heated at 205° C. in diethylaniline, to yield the corresponding Claisen rearrangement adduct 3. The double bond present in 3 is dihydroxylated with $OsO_4$ and glycol 4 is obtained. The dihydroxy system 4 is oxydated with $NaIO_4$ to obtain compound 5, which is mesylated with MsCl to yield 6. This is immediately reacted with triethylamine in ethyl acetate to perform the ring-closing reaction to obtain the benzofurane 7. The nitro group present in 7 is reduced by using iron in HCl/ethanol to yield the corresponding amine 8. The diazonium salt is synthesized with $NaNO_2$ and then it is coupled with 3-ethoxycarbonyl-2-piperidone to yield system 9. The Fisher rearrangement of 9 is carried out by reflux in formic acid and the indole 10 is obtained. The lactam present in 10 is opened by reflux in KOH and the aminoacid 11 thus obtained is decarboxylated in HCl to yield aminoindole XII ($R_1=R_2=R_3=H$, $X=F$). Finally, XII is reacted with several coupling agents to yield final products of general structure I.

Compounds of general structure 11 can be esterified by reacting them with the corresponding alcohols and conventional coupling agents such as carbonyldiimidazole/4-dimethylaminopyridine in N,N-dimethylformamide or dicyclohexylcarbodiimide/4-dimethylaminopyridine in dichloromethane.

Compounds of general structure I can be halogenated in position 2 of indole ring. The most widely used conditions consist in brominating that position by reacting I with bromine in acetic acid. Furthermore the brominated indole compound can be reacted with boronic acids within Suzuki coupling conditions to yield the corresponding Suzuki adducts.

Appropriate coupling agents comprise: a) acyl chlorides of formula $R_4$—COCl, b) chloroformates of formula $R_4$—COCl, and c) isocyanates of formula $R_4$—NO, thus providing compounds of formula I, wherein $R_4$ represents a) linear or branched (1-6C)alkyl, (3-6C)cycloalkyl, $CHFCH_3$, and $CF_3$; b) $OR_6$, wherein $R_6$ is as described herein; and c) $NR_7$, wherein $R_7$ is as described herein, respectively. Subsequent hydrolysis of compounds I, when $R_4$ represents b) $OR_6$ or c) $NHR_7$ provides compounds I, $R_4$ representing b') OH or c') $NH_2$ respectively (Scheme 1').

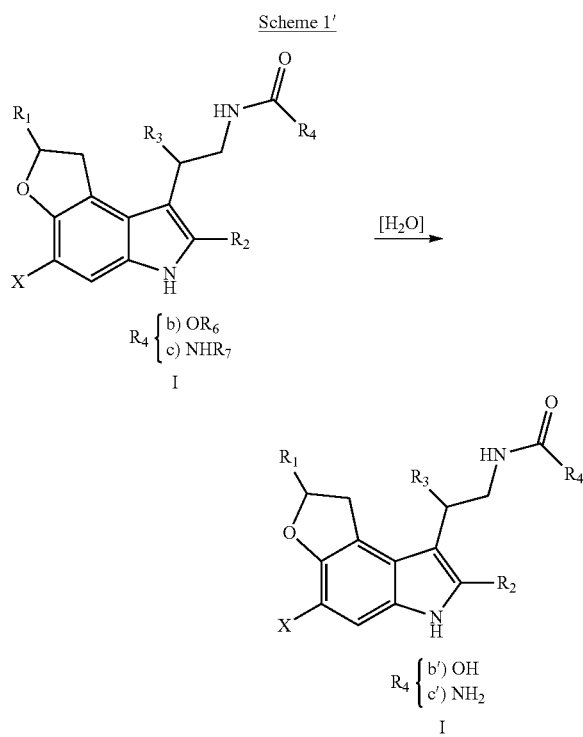

Useful processes for recovering the resultant compounds in step (ii) include conventional methods known to the person skilled in the art such as crystallization and chromatographic processes, resolution of racemic forms by chromatographic separation using a chiral stationary phase, and also processes involving fractional crystallization. This can, in particular, involve the separation of individual enantiomers, for example, diastereoisomeric salts formed with chiral acids, for instance (+)-tartaric acid, (−)-tartaric acid, or (+)-10-camphorsulfonic acid.

The compounds of the present invention can be normally formulated in accordance with standard pharmaceutical practice as a pharmaceutical composition.

The pharmaceutical compositions of this invention may be administered in standard manner for the disease condition that it is desired to treat or prevent, for example by oral, parenteral (i.e. subcutaneous, intramuscular and intravenous), inhalatory or rectal administration. For these purposes the compounds of this invention may be formulated by means known in the art in the form of, for example, tablets, capsules, pills, syrups, aqueous or oily solutions or suspensions, emulsions, dispersible powders, inhalatory solutions, suppositories, drops and sterile aqueous or oily solutions or suspensions for injection, and the like. The pharmaceutical compositions may contain flavoring agents, sweeteners, etc. in suitable solid or liquid carriers or diluents, or in a suitable sterile media to form suspensions or solutions suitable for intravenous, subcutaneous or intramuscular injection. The preferred route of administration of the compounds of the present invention will be the most useful and practical route, most preferably by oral administration. Such compositions typically contain from 0.01 to nearly 100% by weight of active compound of the total weight of the composition, the remainder of the composition being pharmaceutically a suitable carrier.

The active ingredients can be blended with the carrier according to the pharmaceutical technologies well-known to those skilled in the art. Broad class of carriers can be used depending on the pharmaceutical form suitable for administration. Thus, water, glycols, oils, alcohols, flavorings, preservatives, dyes, and mixtures thereof, and the like can be used in oral liquid compositions, such as, for instance, suspensions, solutions, emulsions, aerosols and elixirs. Non-limitative examples of carriers useful for the manufacturing of oral solid compositions include starch, sugars (i.e. lactose, saccharose, sorbitol), celluloses (i.e. hydroxypropyl cellulose, carboxymethyl cellulose, ethyl cellulose, and microcrystalline cellulose), talc, stearic acid, magnesium stearate, phosphoric acid dicalcium salt, gums, copovidone, surfactants (i.e. sorbitan monooleate, and polyethylene glycol), metallic oxides (i.e. titanium dioxide, and ferric oxide), and other carriers such as water, and mixtures thereof. Homogeneous pre-formulations containing the compounds of the present invention are thus prepared. Further, said pre-formulations can be divided in dosage unit forms such as tablets, pills, powders, and capsules, and the like.

Due to their ease of administration, tablets and capsules are the most advantageous dosage unit forms. Tablets can be coated by using conventional aqueous or non aqueous procedures. A broad class of different materials can be used to prepare coatings. Such materials include a great variety of polymeric acids, and mixtures thereof, with some other components such as, for instance, shellac, cetyl alcohol, and cellulose acetate.

Non-limitative liquid forms wherein the compounds of the present invention can be incorporated for oral or injection administration routes include aqueous solutions, capsules filled with liquid or gel, syrups with flavorings, aqueous suspensions, oily suspensions, emulsions flavored with edible oils, such as, for instance, olive oil, cotton oil, sesame oil, coconut oil, peanut oil, as well as elixirs, and similar pharmaceutical carriers, and mixtures thereof. Suitable diluents for the preparation of suspensions include synthetic gums, natural gums, such as, for instance, tragacanth, acacia, xanthan, and guar, alginates, dextrans, sodium carboxymethyl cellulose, methylcellulose, polyethylene glycol, polyvinylpyrrolidone, and gelatin, and mixtures thereof.

The dose of the composition varies, depending on the subject to which the composition is administered, the administration route, the condition, etc. For example, when the composition is administered to an adult patient suffering from sleep disorders, it is preferable to administer once daily or divided in several doses in an amount of approximately 0.0005 to 2 mg/kg body weight, preferably approximately 0.001 to 1 mg/kg body weight, more preferably approximately 0.001 to 0.5 mg/kg body weight, in terms of the amount of the active ingredient, compound I.

Throughout the description and claims the word "comprise" and variations of the word, such as "comprising", are not intended to exclude other technical features, additives, components, or steps. Additional objects, advantages and features of the invention will become apparent to those skilled in the art upon examination of the description or may be learned by practice of the invention. The following examples are provided by way of illustration, and are not intended to be limiting of the present invention.

EXAMPLES

Example 1

1-Allyloxy-2-fluoro-4-nitro-benzene, 2

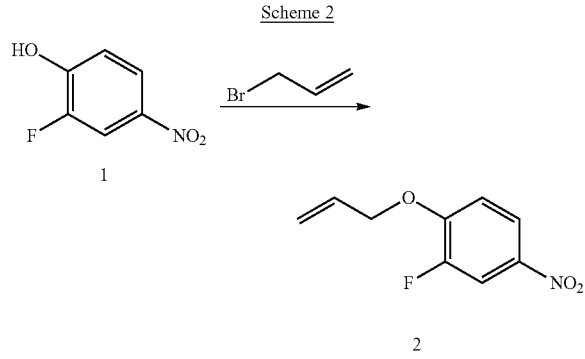

A solution of compound 1 (20 g, 127.3 mmol), allyl bromide (16.19 mL, 190.96 mmol) and potassium carbonate (44 g, 318.25 mmol) in acetone (300 mL) was refluxed overnight. The solvent was removed in vacuo. The residue obtained was suspended in water and extracted with ethyl acetate. The organic layer was dried over anhydrous sodium sulphate. The filtrate was concentrated to yield the desired compound 2 (25 g, yield 99.6%).

HPLC-MS: Purity 99.9%, M+1=198

Example 2

2-Allyl-6-fluoro-4-nitro-phenol, 3

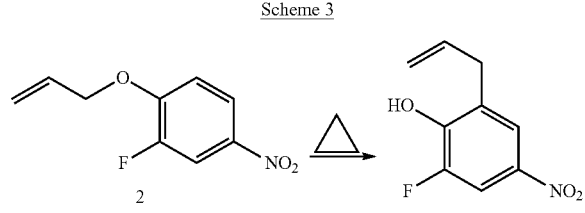

Compound 2 (25 g, 126.8 mmol) was solved in diethyl aniline (150 mL, 937.7 mmol) and the resulting solution was refluxed for 48 h. The crude was evaporated in vacuo and the residue was purified by column chromatography, eluted at 10% ethyl acetate/hexane. Fractions were collected to obtain the desired compound 3 (15 g, yield 60%).

HPLC-MS: Purity 99.9%, M+1=198

Example 3

3-(3-Fluoro-2-hydroxy-5-nitro-phenyl)-propane-1,2-diol, 4

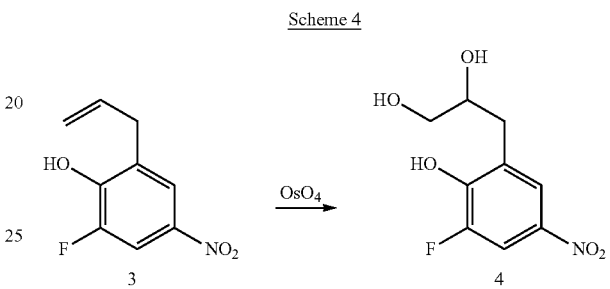

N-methylmorpholine N-oxide (2.7 g, 23 mmol) was added to a suspension of Compound 3 (4.55 g, 23 mmol) in 50 mL of acetone/water (10:1) at 0° C. After 7 min $OsO_4$ (1.048 mL, 0.092 mmol) was added slowly. The solution was stirred 36 h at room temperature, and then the solvent was evaporated in vacuo. It was acidified with dilute hydrochloric acid and extracted with ethyl acetate. The filtrate was concentrated to yield the corresponding compound 4 (5.1 g, yield 85.2%).

HPLC-MS: Purity 97%, M+1=232

Example 4

2-Fluoro-6-(2-hydroxy-ethyl)-4-nitro-phenol, 5

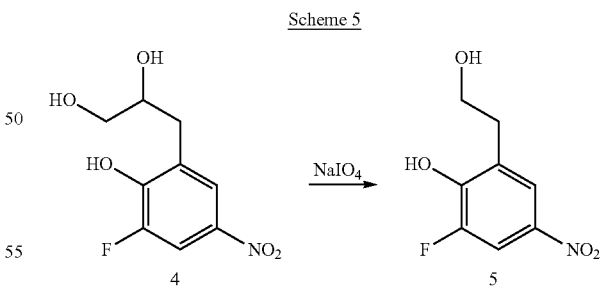

Compound 4 (3.7 g, 16 mmol) was suspended in water and dissolved by adding a few drops of acetone. $NaIO_4$ (3.42 g, 16 mmol) was added portionwise at 0° C. After 7 min $NaBH_4$ (4.84 g, 128 mmol) was added slowly. The solution was stirred for 1 h at room temperature, the acidified with dilute hydrochloric acid and extracted with ethyl acetate. The filtrate was concentrated to yield the desired compound 5 (2.4 g, yield 75%).

HPLC-MS: Purity 98%, M+1=202

Example 5

Methanesulfonic acid 2-(3-fluoro-2-hydroxy-5-nitro-phenyl)-ethyl ester, 6

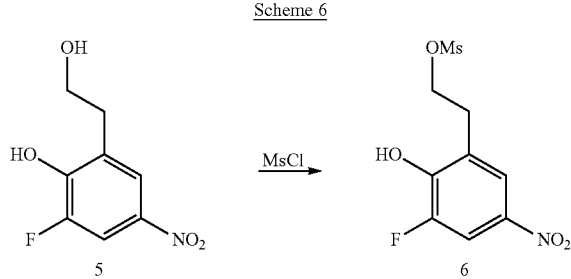

Scheme 6

Methanesulfonyl chloride (1.39 mL, 18.0 mmol) was added dropwise to a stirred solution of the alcohol 5 (3.62 g, 18.0 mmol) in pyridine (14.6 mL, 180 mmol) at −10° C. After stirring for 25 min an additional quantity of methanesulfonyl chloride (0.697 mL, 9.0 mmol) was added and the reaction mixture was further stirred for 30 min at −10° C. A mixture of ethyl acetate and saturated $NaHCO_3$ (10 mL) solution were slowly added to the above solution at 0° C. It was stirred 30 min at room temperature, the water was added and the crude was slightly acidified with dilute HCl and then extracted with ethyl acetate. The organic layer was concentrated to obtain the crude mesylate compound 6 (3.5 g), which was used immediately for the next step.

Example 6

7-Fluoro-5-nitro-2,3-dihydro-benzofuran, 7

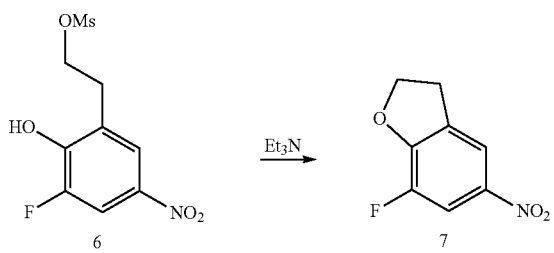

Scheme 7

A suspension of 6 (3.5 g, 12.53 mmol) in ethyl acetate (45 mL) and triethyl amine (4.37 mL, 31.33 mmol) was refluxed overnight. Water was added and the crude was extracted with ethyl acetate. The organic layer was concentrated, purified by column chromatography eluted with 15% ethyl acetate/hexane, to yield the desired compound 7 (1.4 g, yield 61%).

HPLC-MS: Purity 99.9%, M+1=184

Example 7

7-Fluoro-2,3-dihydro-benzofuran-5-ylamine, 8

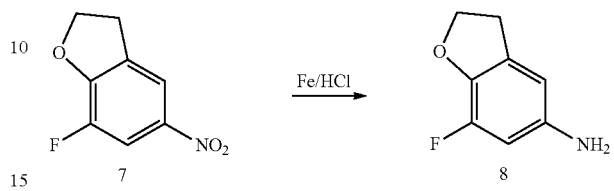

Scheme 8

Compound 7 (1.4 g, 7.64 mmol) was suspended in ethanol (51 mL). Iron (2.57 g, 45.85 mmol) and conc. HCl (4 mL) was added at 0° C. The resulting suspension was stirred overnight at room temperature. The reaction was quenched by addition of $NaHCO_3$. The crude was extracted with ethyl acetate. It was purified by column chromatography, eluted at 25% ethyl acetate/hexane, to yield the desired compound 8 (1.09 g, yield 93.1%).

HPLC-MS: Purity 99.9%, M+1=154

Example 8

3-[(7-Fluoro-2,3-dihydro-benzofuran-5-yl)-hydrazono]-piperidin-2-one, 9

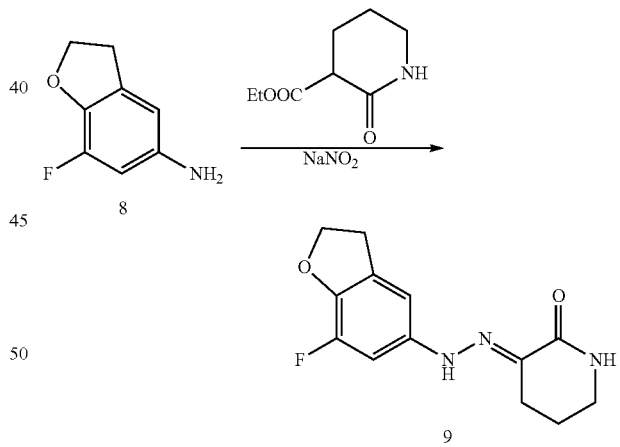

Scheme 9

Fluoro-benzo-furan-amine 8 (1.0 g, 6.527 mmol) was suspended with water (12.55 mL) and concentrated HCl (1.5 mL) was added. The mixture was cooled in an ice bath and a solution of 200 mg $NaNO_2$ in water (12.55 mL) was added dropwise and the mixture was stirred for 30 min. The pH of the solution (Solution A) was adjusted to 4.5 with a 10% solution of $Na_2CO_3$. Ethyl-2-oxo-5-methylpiperidine-3-carboxylate (1.19 g, 6.527 mmol) was dissolved in water (12.55 mL) containing potassium hydroxide (0.35 g, 6.25 mmol). The solution was stirred at room temperature overnight. This solution was then cooled in an ice bath and was treated with a solution of fluoro-benzo-furan diazonium chloride (Solution A). The pH of the resulting solution was adjusted to pH 5 by the addition of acetic acid. Stirring was continued for 4 h at 0° C. and kept overnight at freeze. The solid obtained was filtered to yield the desired compound 9 (500 mg, yield 29%).

HPLC-MS: Purity 98%, M+1=264

Example 9

4-Fluoro-1,2,6,8,9,10-hexahydro-3-oxa-6,8-diaza-cyclopenta[c]fluoren-7-one, 10

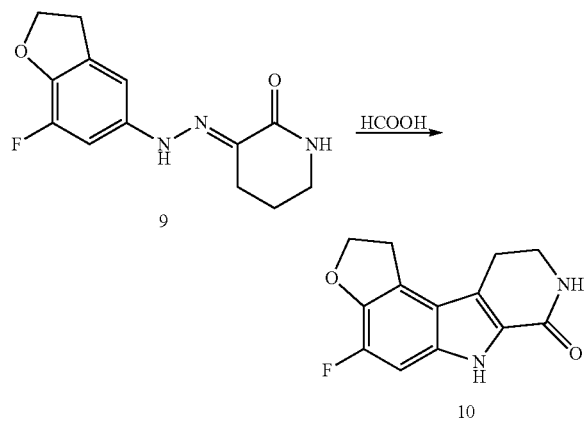

Diazotized compound 9 (500 mg, 1.89 mmol) was solved in 8.25 mL formic acid (90%) and the solution was heated at reflux for 1 h. The reaction was allowed to cool and 10 mL of water were added. The resulting mixture was extracted with ethyl acetate. The organic layer was concentrated to obtain the desired compound 10 (270 mg, yield 57%).

HPLC-MS: Purity 98%, M+1=247

Example 10

8-(2-Amino-ethyl)-4-fluoro-1,6-dihydro-2H-3-oxa-6-aza-as-indacene-7-carboxylic acid, 11

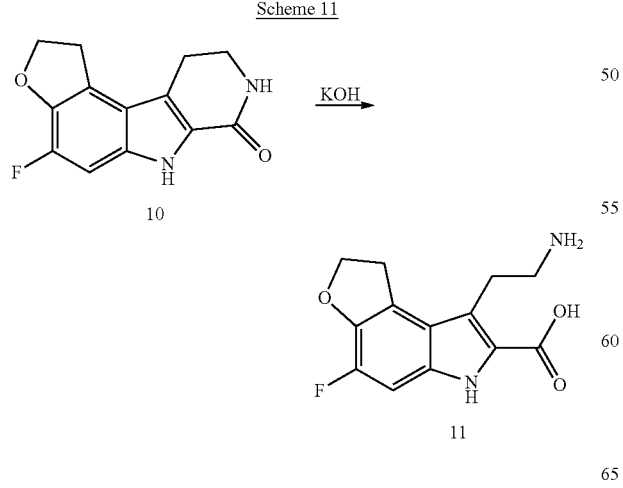

To a stirring solution of KOH (214 mg, 3.82 mmol) in ethanol (50%), compound 10 (108 mg, 0.438 mmol) was added. It was refluxed for 6 h and kept overnight at room temperature. The solvent was removed and water was added to the residue thus obtained. It was filtered and acidified with acetic acid. The solid obtained was washed with water. The filtrate was again extracted with ethyl acetate. The organic layer was concentrated to yield the desired compound 11 (55 mg, yield 47.45%).

HPLC-MS: Purity 99.9%, M+1=265

Example 11

2-(4-Fluoro-1,6-dihydro-2H-3-oxa-6-aza-as-indacen-8-yl)-ethylamine, XII ($R_1=R_2=R_3=H$, $X=F$)

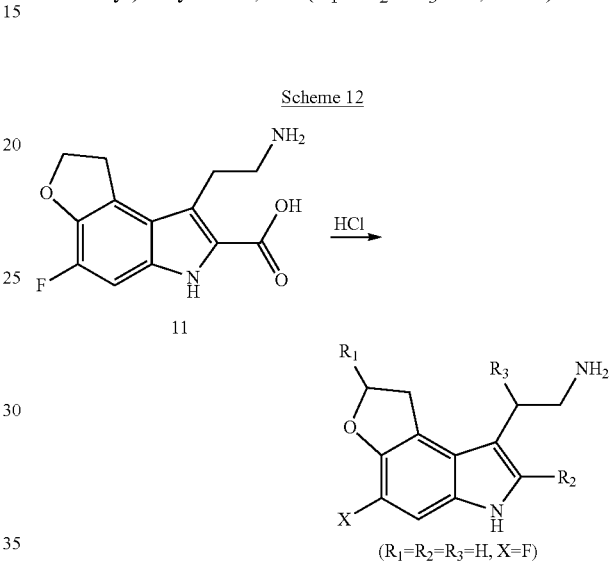

Compound 11 (55 mg, 0.208 mmol) was refluxed with 10% HCl for 2 h. After cooling the resulting solution was made alkaline with 30% NaOH. It was extracted with ethyl acetate. The organic layer was concentrated to yield the desired compound, 2-(4-fluoro-1,6-dihydro-2H-3-oxa-6-aza-as-indacen-8-yl)-ethylamine (XII, $R_1=R_2=R_3=H$, $X=F$, 23 mg, yield 50%).

HPLC-MS: Purity 99.9%, M+1=221

Example 12

N-[2-(4-Fluoro-1,6-dihydro-2H-3-oxa-6-aza-as-indacen-8-yl)-ethyl]-carboxamides, (I, 13-43)

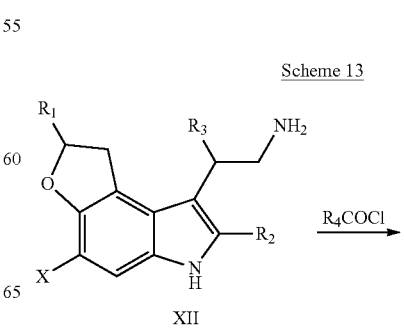

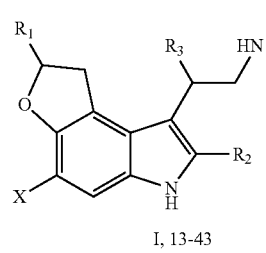

I, 13-43

To a stirred suspension of amine derivative XII (54 mg, 0.245 mmol) in dry dichloromethane (5 mL) at 0° C., triethylamine (0.051 mL, 0.367 mmol) and corresponding carbonyl chloride (0.245 mmol) ($R_4COCl$) were added. The reaction mixture was kept at room temperature overnight. The crude was quenched by adding water and extracted with dichloromethane. The organic layer was concentrated and purified by column chromatography (flash silica gel), eluted at the range of 60 to 70% ethyl acetate/hexane to yield the desired carboxamide compound (I, 13-43) (yield: 80 to 97%).

Compounds 13-43 thus obtained from the appropriate acyl chlorides are summarized in Table 1.

TABLE 1

Compounds I (13-43)

| | Compound I | $R_1$ | $R_2$ | $R_3$ | $R_4$ | X | Purity (%) | LCMS M + 1 |
|---|---|---|---|---|---|---|---|---|
| 13 | N-[2-(4-Fluoro-1,6-dihydro-2H-3-oxa-6-aza-as-indacen-8-yl)-ethyl]-acetamide | H | H | H | Me | F | 96.76 | 263 |
| 14 | N-[2-(4-Fluoro-1,6-dihydro-2H-3-oxa-6-aza-as-indacen-8-yl)-ethyl]-propionamide | H | H | H | Et | F | 93.33 | 277 |
| 15 | N-[2-(4-Fluoro-1,6-dihydro-2H-3-oxa-6-aza-as-indacen-8-yl)-ethyl]-butiramide | H | H | H | Pr | F | 90.49 | 291 |
| 16 | N-[2-(4-Fluoro-1,6-dihydro-2H-3-oxa-6-aza-as-indacen-8-yl)-ethyl]-isobutyramide | H | H | H | iPr | F | 88.23 | 291 |
| 17 | Cyclopropanecarboxylic acid [2-(4-fluoro-1,6-dihydro-2H-3-oxa-6-aza-as-indacen-8-yl)-ethyl]-amide | H | H | H | cPr | F | 90.29 | 289 |
| 18 | 2,2,2-Trifluoro-N-[2-(4-fluoro-1,6-dihydro-2H-3-oxa-6-aza-as-indacen-8-yl)-ethyl]-acetamide | H | H | H | $CF_3$ | F | 82.95 | 317 |
| 19 | N-[2-(4-Fluoro-2-methyl-1,6-dihydro-2H-3-oxa-6-aza-as-indacen-8-yl)-propyl]-butyramide | Me | H | Me | Pr | F | 98.36 | 319.4 |
| 20 | N-[2-(4-Fluoro-2-methyl-1,6-dihydro-2H-3-oxa-6-aza-as-indacen-8-yl)-propyl]-propionamide | Me | H | Me | Et | F | 98.19 | 305.4 |
| 21 | N-[2-(4-Fluoro-2-methyl-1,6-dihydro-2H-3-oxa-6-aza-as-indacen-8-yl)-propyl]-acetamide | Me | H | Me | Me | F | 96.71 | 291.3 |
| 22 | N-[2-(4-Fluoro-2-methyl-1,6-dihydro-2H-3-oxa-6-aza-as-indacen-8-yl)-ethyl]-acetamide | Me | H | H | Me | F | 96.95 | 277.3 |
| 23 | N-[2-(4-Fluoro-2-methyl-1,6-dihydro-2H-3-oxa-6-aza-as-indacen-8-yl)-ethyl]-propionamide | Me | H | H | Et | F | 97.90 | 291.3 |
| 24 | N-[2-(4-Fluoro-2-methyl-1,6-dihydro-2H-3-oxa-6-aza-as-indacen-8-yl)-ethyl]-butyramide | Me | H | H | Pr | F | 99.59 | 305.4 |
| 25 | Pentanoic acid [2-(4-fluoro-2-methyl-1,6-dihydro-2H-3-oxa-6-aza-as-indacen-8-yl)-ethyl]-amide | Me | H | H | Bu | F | 99.21 | 319.4 |
| 26 | N-[2-(4-Fluoro-2-methyl-1,6-dihydro-2H-3-oxa-6-aza-as-indacen-8-yl)-ethyl]-isobutyramide | Me | H | H | iPr | F | 95.68 | 305.4 |
| 27 | Cyclopropanecarboxylic acid [2-(4-fluoro-2-methyl-1,6-dihydro-2H-3-oxa-6-aza-as-indacen-8-yl)-ethyl]-amide | Me | H | H | cPr | F | 95.83 | 303.3 |
| 28 | 2,2,2-Trifluoro-N-[2-(4-fluoro-2-methyl-1,6-dihydro-2H-3-oxa-6-aza-as-indacen-8-yl)-ethyl]-acetamide | Me | H | H | CF3 | F | 99.18 | 331.3 |
| 29 | [2-(4-Fluoro-2-methyl-1,6-dihydro-2H-3-oxa-6-aza-as-indacen-8-yl)-ethyl]-carbamic acid methyl ester | Me | H | H | OMe | F | 97.67 | 293.3 |

TABLE 1-continued

Compounds I (13-43)

| | Compound I | R₁ | R₂ | R₃ | R₄ | X | Purity (%) | LCMS M + 1 |
|---|---|---|---|---|---|---|---|---|
| 30 | [2-(4-Fluoro-2-methyl-1,6-dihydro-2H-3-oxa-6-aza-as-indacen-8-yl)-ethyl]-carbamic acid ethyl ester | Me | H | H | OEt | F | 96.40 | 307.3 |
| 31 | N-[2-(4-Fluoro-2-methyl-1,6-dihydro-2H-3-oxa-6-aza-as-indacen-8-yl)-ethyl]-3-methyl-butyramide | Me | H | H | iBu | F | 98.49 | 319.4 |
| 32 | 2-Fluoro-N-[2-(4-fluoro-2-methyl-1,6-dihydro-2H-3-oxa-6-aza-as-indacen-8-yl)-ethyl]-propionamide | Me | H | H | CH3CHF | F | 97.38 | 309.3 |
| 33 | 1-Ethyl-3-[2-(4-fluoro-2-methyl-1,6-dihydro-2H-3-oxa-6-aza-as-indacen-8-yl)-ethyl]-urea | Me | H | H | NHEt | F | 99.75 | 306.4 |
| 34 | N-[2-(4-Fluoro-2-methyl-1,6-dihydro-2H-3-oxa-6-aza-as-indacen-8-yl)-propyl]-isobutyramide | Me | H | Me | iPr | F | 98.97 | 319.4 |
| 35 | Cyclopropanecarboxylic acid [2-(4-fluoro-2-methyl-1,6-dihydro-2H-3-oxa-6-aza-as-indacen-8-yl)-propyl]-amide | Me | H | Me | cPr | F | 97.85 | 317.4 |
| 36 | N-[2-(4-Fluoro-2-methyl-1,6-dihydro-2H-3-oxa-6-aza-as-indacen-8-yl)-propyl]-3-methyl-butyramide | Me | H | Me | iBu | F | 99.19 | 333.4 |
| 37 | N-[2-(4-Fluoro-2-methyl-1,6-dihydro-2H-3-oxa-6-aza-as-indacen-8-yl)-propyl]-2,2-dimethyl-propionamide | Me | H | Me | tBu | F | 98.38 | 333.4 |
| 38 | 2,2,2-Trifluoro-N-[2-(4-fluoro-2-methyl-1,6-dihydro-2H-3-oxa-6-aza-as-indacen-8-yl)-propyl]-acetamide | Me | H | Me | CF3 | F | 96.26 | 345.3 |
| 39 | Pentanoic acid [2-(4-fluoro-2-methyl-1,6-dihydro-2H-3-oxa-6-aza-as-indacen-8-yl)-propyl]-amide | Me | H | Me | Bu | F | 99.37 | 333.4 |
| 40 | [2-(4-Fluoro-2-methyl-1,6-dihydro-2H-3-oxa-6-aza-as-indacen-8-yl)-propyl]-carbamic acid methyl ester | Me | H | Me | OMe | F | 96.31 | 307.3 |
| 41 | [2-(4-Fluoro-2-methyl-1,6-dihydro-2H-3-oxa-6-aza-as-indacen-8-yl)-propyl]-carbamic acid ethyl ester | Me | H | Me | OEt | F | 95.57 | 321.4 |
| 42 | 1-Ethyl-3-[2-(4-fluoro-2-methyl-1,6-dihydro-2H-3-oxa-6-aza-as-indacen-8-yl)-propyl]-urea | Me | H | Me | NHEt | F | 98.30 | 320.4 |
| 43 | 2-Fluoro-N-[2-(4-fluoro-2-methyl-1,6-dihydro-2H-3-oxa-6-aza-as-indacen-8-yl)-propyl]-propionamide | Me | H | Me | CH3CHF | F | 96.97 | 323.4 |

Example 13

In Vitro MT1 Screening

To proceed with compound screening over MT1 receptor, a cell line characterised by a stable overexpression of recombinant human-MT1 receptor was used. This line co-expresses mitochondrial apoaequorin and subunit Gα16.

Subunit Gα16 belongs to GPCR superfamily, in which intracellular signal transduction is produced via phospholipase (PLC). Activation of PLC produces an increment of inositol-triphosphate levels and intracellular calcium levels. This increment in calcium levels is, therefore, independent and full compatible with the signal transduction of MT1 receptor.

Apoaequorin is the inactive form of aequorin, a phosphoprotein that needs a prosthethic hydrophobic group, colenterazine, to achieve active forms. After binding to calcium, aequorin carries out the oxidation of colenterazine to colenteramide, a luminescent reaction.

Assay protocol for agonist screening consists in an overnight incubation of cells and colenterazine, being performed by an AequoScreen™ system instrument, PerkinElmer, USA. After that this mixture was injected over a plate that contains the solution of the compounds to screen and luminescence was immediately read. Only in case of antagonism screening, after 15-30 min of the first injection the reference agonist was added in the same well, and then luminescence was measured.

Agonist activity was calculated as percentage of activity relative to the reference agonist at the $EC_{100}$ concentration.

Activity of antagonists was expressed as the inhibition percentage over the activity of reference agonist at its $EC_{80}$, concentration. Table 2 summarizes the agonism % of MT1 receptor of compounds (I, 13-43).

TABLE 2

Agonism percentages of MT1 (at 100 nM and 1 nM concentrations)

| | | | Compound | | | MT1 | |
|---|---|---|---|---|---|---|---|
| I | $R_1$ | $R_2$ | $R_3$ | $R_4$ | X | 100 nM | 1 nM |
| 13 | H | H | H | Me | F | 92.9 | 37.7 |
| 14 | H | H | H | Et | F | 101.7 | 55.1 |
| 15 | H | H | H | Pr | F | 108.2 | 43.0 |
| 16 | H | H | H | iPr | F | 82.3 | 23.0 |
| 17 | H | H | H | cPr | F | 93.2 | 43.8 |
| 18 | H | H | H | $CF_3$ | F | 104.6 | 59.8 |
| 19 | Me | H | Me | Pr | F | 96.8 | 27.8 |
| 20 | Me | H | Me | Et | F | 94.3 | 30.2 |
| 21 | Me | H | Me | Me | F | 92.6 | 43.2 |
| 22 | Me | H | H | Me | F | 96.8 | 50.5 |
| 23 | Me | H | H | Et | F | 99.7 | 39.1 |
| 24 | Me | H | H | Pr | F | 99.8 | 42.1 |
| 25 | Me | H | H | Bu | F | 98 | 31.9 |
| 26 | Me | H | H | iPr | F | 84.8 | 25.7 |
| 27 | Me | H | H | cPr | F | 91.1 | 33.8 |
| 28 | Me | H | H | $CF_3$ | F | 97.2 | 36.1 |
| 29 | Me | H | H | OMe | F | 77.3 | 17.4 |
| 30 | Me | H | H | OEt | F | 68.1 | 7.1 |
| 31 | Me | H | H | iBu | F | 90.4 | 22.3 |
| 32 | Me | H | H | $CH_3CHF$ | F | 93.1 | 38.6 |
| 33 | Me | H | H | NHEt | F | 87.5 | 26.6 |
| 34 | Me | H | Me | iPr | F | 95.8 | 18.4 |
| 35 | Me | H | Me | cPr | F | 94 | 30.5 |
| 36 | Me | H | Me | iBu | F | 89.7 | 20.9 |
| 37 | Me | H | Me | tBu | F | 52.8 | 6.6 |
| 38 | Me | H | Me | $CF_3$ | F | 101 | 36.9 |
| 39 | Me | H | Me | Bu | F | 91.4 | 24.6 |
| 40 | Me | H | Me | OMe | F | 95.2 | 24 |
| 41 | Me | H | Me | OEt | F | 78.9 | 13.1 |
| 42 | Me | H | Me | NHEt | F | 87.8 | 19.7 |
| 43 | Me | H | Me | $CH_3CHF$ | F | 92.8 | 30.6 |
| | | | | Ramelteon | | 117.5 | 47.4 |
| | | | | Melatonin | | 102.6 | 48.0 |

The invention claimed is:
1. A compound of formula I,

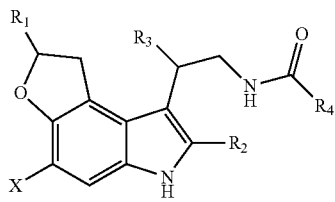

in free or pharmaceutically acceptable salt, or enantiomeric form, wherein:
$R_1$ is selected from the group consisting of hydrogen, linear or branched (1-6C)alkyl, and (3-6C)cycloalkyl;
$R_2$ is selected from the group consisting of hydrogen, chlorine, bromine, phenyl, phenyl(1-2C)alkyl, COOH, and $COOR_5$;
$R_3$ is selected from the group consisting of hydrogen, linear or branched (1-6C)alkyl, and (3-6C)cycloalkyl;
$R_4$ is selected from the group consisting of linear or branched (1-6C)alkyl, (3-6C)cycloalkyl, $CHFCH_3$, $CF_3$, OH, $OR_6$, $NH_2$, and $NHR_7$;
$R_5$ is selected from the group consisting of linear or branched (1-6C)alkyl, phenyl, phenyl(1-2C)alkyl, and (3-6C)cycloalkyl;
$R_6$ is selected from the group consisting of linear or branched (1-6C)alkyl, and (3-6C)cycloalkyl;
$R_7$ is selected from the group consisting of linear or branched (1-6C)alkyl, and (3-6C)cycloalkyl; and
X is a halogen atom selected from the group consisting of fluorine, and chlorine.

2. The compound according to claim 1, wherein $R_1$ is selected from the group consisting of hydrogen and methyl.

3. The compound according to claim 1, wherein $R_2$ is hydrogen.

4. The compound according to claim 1, wherein $R_3$ is selected from the group consisting of hydrogen and methyl.

5. The compound according to claim 1, wherein $R_4$ is selected from the group consisting of methyl, ethyl, propyl, i-propyl, butyl, c-propyl, $CF_3$, and $CHFCH_3$.

6. The compound according to claim 1, wherein $R_5$ is methyl.

7. The compound according to claim 1, wherein $R_6$ is selected from the group consisting of methyl and ethyl.

8. The compound according to claim 1, wherein $R_7$ is selected from the group consisting of methyl and ethyl.

9. The compound according to claim 1, wherein X is fluorine.

10. The compound as claimed in claim 1, which is selected from the group consisting of
N-[2-(4-Fluoro-1,6-dihydro-2H-3-oxa-6-aza-as-indacen-8-yl)-ethyl]-acetamide;
N-[2-(4-Fluoro-1,6-dihydro-2H-3-oxa-6-aza-as-indacen-8-yl)-ethyl]-propionamide;
N-[2-(4-Fluoro-1,6-dihydro-2H-3-oxa-6-aza-as-indacen-8-yl)-ethyl]-butyramide;
N-[2-(4-Fluoro-1,6-dihydro-2H-3-oxa-6-aza-as-indacen-8-yl)-ethyl]-isobutyramide;
Cyclopropanecarboxylic acid [2-(4-fluoro-1,6-dihydro-2H-3-oxa-6-aza-as-indacen-8-yl)-ethyl]-amide;
2,2,2-Trifluoro-N-[2-(4-fluoro-1,6-dihydro-2H-3-oxa-6-aza-as-indacen-8-yl)-ethyl]-acetamide;
N-[2-(4-Fluoro-2-methyl-1,6-dihydro-2H-3-oxa-6-aza-as-indacen-8-yl)-propyl]-propionamide;
N-[2-(4-Fluoro-2-methyl-1,6-dihydro-2H-3-oxa-6-aza-as-indacen-8-yl)-propyl]-acetamide;
N-[2-(4-Fluoro-2-methyl-1,6-dihydro-2H-3-oxa-6-aza-as-indacen-8-yl)-ethyl]-acetamide;
N-[2-(4-Fluoro-2-methyl-1,6-dihydro-2H-3-oxa-6-aza-as-indacen-8-yl)-ethyl]-propionamide;
N-[2-(4-Fluoro-2-methyl-1,6-dihydro-2H-3-oxa-6-aza-as-indacen-8-yl)-ethyl]-butyramide;
Pentanoic acid [2-(4-fluoro-2-methyl-1,6-dihydro-2H-3-oxa-6-aza-as-indacen-8-yl)-ethyl]-amide;
Cyclopropanecarboxylic acid [2-(4-fluoro-2-methyl-1,6-dihydro-2H-3-oxa-6-aza-as-indacen-8-yl)-ethyl]-amide;
2,2,2-Trifluoro-N-[2-(4-fluoro-2-methyl-1,6-dihydro-2H-3-oxa-6-aza-as-indacen-8-yl)-ethyl]-acetamide;
2-Fluoro-N-[2-(4-fluoro-2-methyl-1,6-dihydro-2H-3-oxa-6-aza-as-indacen-8-yl)-ethyl]-propionamide;
Cyclopropanecarboxylic acid [2-(4-fluoro-2-methyl-1,6-dihydro-2H-3-oxa-6-aza-as-indacen-8-yl)-propyl]-amide;
2,2,2-Trifluoro-N-[2-(4-fluoro-2-methyl-1,6-dihydro-2H-3-oxa-6-aza-as-indacen-8-yl)-propyl]-acetamide, and
2-Fluoro-N-[2-(4-fluoro-2-methyl-1,6-dihydro-2H-3-oxa-6-aza-as-indacen-8-yl)-propyl]-propionamide.

11. A process for preparing a compound of formula I as defined in claim 1 in free or pharmaceutically acceptable salt, or an enantiomeric form, which method comprises:
i) a) reacting a compound of formula XII,

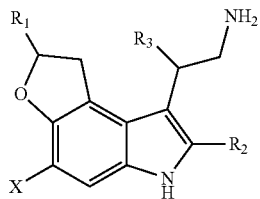

wherein $R_1$, $R_2$, $R_3$, and X are as defined in any one of claims 1 to 8, with a coupling agent selected from the group consisting of: a) an acyl chloride of formula $R_4$—COCl, in which case $R_4$ represents linear or branched (1-6C)alkyl, (3-6C)cycloalkyl, CHFCH$_3$, or CF$_3$; b) a chloroformate of formula $R_4$—COCl, in which case $R_4$ represents OR$_6$, wherein $R_6$ is as defined in any one of claims 1 to 8; and c) an isocyanate of formula $R_4$=CO, in which case $R_4$ represents NR$_7$, wherein $R_7$ is as defined in any one of claims 1 to 8; and
b) hydrolyzing, if desired, the resultant compound of formula I when $R_4$ is OR$_6$ or NHR$_7$ to OH or NH$_2$ respectively; and
ii) recovering the resultant compound of formula I in free or pharmaceutically acceptable salt or enantiomeric form thereof.

12. A pharmaceutical composition comprising a therapeutically effective amount of the compound of formula I as defined in claim 1, and a suitable carrier.

13. A medicament which comprises the compound of formula I as defined in claim 1.

14. A method for the treatment of conditions associated with a disturbed functioning of systems regulated by melatonin, which method comprises administering a compound of formula I as defined in claim 1 to a subject in need thereof.

15. The method of claim 14, wherein the conditions associated with a disturbed functioning of systems regulated by melatonin is selected from the group consisting of depression, stress, sleep disorders, anxiety, cardiovascular pathology, pathology of the digestive system, schizophrenia, panic attack, melancholia, appetite disorders, obesity, psychotic disorders, epilepsy, diabetes, Parkinson's disease, senile dementia, disorders associated with normal or pathological ageing, migraine, memory loss, Alzheimer's disease and cerebral circulation disorders.

16. The method of claim 14, wherein the condition associated with a disturbed functioning of systems regulated by melatonin is selected from the group consisting of sleep disorders and depression.

17. The method of claim 14, wherein the sleep disorder is insomnia.

18. The method according to claim 14, wherein the sleep disorder is insomnia due to jetlag or fatigue due to jetlag.

19. The method according to claim 14, wherein the depression is a seasonal affective disorder.

* * * * *